United States Patent
Sasaki et al.

(10) Patent No.: US 9,789,042 B2
(45) Date of Patent: Oct. 17, 2017

(54) DAMAGED HAIR IMPROVING AGENT AND PROCESS FOR IMPROVING DAMAGED HAIR USING THE SAME

(75) Inventors: Naoki Sasaki, Narita (JP); Yuki Kokeguchi, Narita (JP); Kiyotaka Kawai, Narita (JP)

(73) Assignee: Kokyu Alcohol Kogyo Co., Ltd., Chiba (JP)

( * ) Notice: Subject to any disclaimer, the term of this patent is extended or adjusted under 35 U.S.C. 154(b) by 487 days.

(21) Appl. No.: 13/430,061

(22) Filed: Mar. 26, 2012

(65) Prior Publication Data

US 2012/0244100 A1    Sep. 27, 2012

Related U.S. Application Data

(60) Provisional application No. 61/467,476, filed on Mar. 25, 2011.

(51) Int. Cl.

| | | |
|---|---|---|
| *A61K 8/37* | (2006.01) | |
| *A61Q 5/00* | (2006.01) | |
| *A61K 8/92* | (2006.01) | |
| *A61K 8/31* | (2006.01) | |
| *A61K 8/34* | (2006.01) | |
| *A61K 8/36* | (2006.01) | |
| *A61Q 5/02* | (2006.01) | |
| *A61Q 5/06* | (2006.01) | |

(52) U.S. Cl.
CPC .......... *A61K 8/37* (2013.01); *A61K 8/31* (2013.01); *A61K 8/345* (2013.01); *A61K 8/361* (2013.01); *A61K 8/375* (2013.01); *A61Q 5/002* (2013.01); *A61Q 5/02* (2013.01); *A61Q 5/06* (2013.01)

(58) Field of Classification Search
USPC ........................................................ 560/186
See application file for complete search history.

(56) References Cited

U.S. PATENT DOCUMENTS

| | | | | |
|---|---|---|---|---|
| 8,367,084 | B2 * | 2/2013 | Arahira et al. | 424/401 |
| 8,420,109 | B2 * | 4/2013 | Sasaki et al. | 424/401 |
| 2006/0013783 | A1 * | 1/2006 | Sebillotte-Arnaud et al. | 424/70.1 |
| 2006/0083703 | A1 * | 4/2006 | Torgerson | 424/70.11 |
| 2007/0110702 | A1 | 5/2007 | Ehara | |
| 2010/0324136 | A1 * | 12/2010 | Arahira et al. | 514/547 |
| 2011/0034723 | A1 * | 2/2011 | Sasaki et al. | 560/186 |

FOREIGN PATENT DOCUMENTS

| | | |
|---|---|---|
| JP | 2006-111543 | 4/2006 |
| JP | 2007-161605 | 6/2007 |
| JP | 2007-223930 | 9/2007 |
| JP | 2009-051817 | 3/2009 |
| JP | 2009-221143 | 10/2009 |
| WO | WO-2006/003992 | 1/2006 |

* cited by examiner

*Primary Examiner* — Bethany Barham
*Assistant Examiner* — Dominic Lazaro
(74) *Attorney, Agent, or Firm* — Norris McLaughlin & Marcus, P.A.

(57) ABSTRACT

The present invention relates to a damaged hair improving agent, comprising: (A) an ester compound made from dipentaerythritol and at least one fatty acid selected from the group consisting of fatty acids having 5 to 16 carbon atoms, wherein the molar ratio of dipentaerythritol residue to the fatty acid (having 5 to 16 carbon atoms) residue ranges from 1.0:3.0 to 1.0:6.0, and one or more substances selected from the group consisting of (B) an ester compound having a linear or branched alkyl or alkenyl group having 16 to 18 carbon atoms wherein hydrogen atoms on these groups are optionally replaced with hydroxyl groups, and a viscosity of 2,000 mPa·s or less at 25° C. (exclusive of the component (A)), (C) an alcohol having a linear or branched alkyl or alkenyl group having 16 to 18 carbon atoms and a viscosity of 2,000 mPa·s or less at 25° C., and (D) hydrocarbon oil having at least 20 carbon atoms. The damaged hair improving agent imparts sleek fell to damaged hair and reduces gritty feel of the damaged hair to impart smooth feel to the damaged hair.

10 Claims, No Drawings

DAMAGED HAIR IMPROVING AGENT AND PROCESS FOR IMPROVING DAMAGED HAIR USING THE SAME

TECHNICAL FIELD

The present invention relates to a damaged hair improving agent and a process for improving damaged hair using the same.

BACKGROUND ART

In recent years, hair damage, which is caused by chemical treatment with, for example, a hair dyeing agent and a perming agent or physical treatment such as friction and heat, has became a significant problem. A major concern is how to improve the damaged hair. To improve damaged hair means to repair dried-out hair having poor "finger-combability" by imparting sleekness and smoothness to the hair to achieve excellent finger-combability with no dried-out feel.

Traditionally, a known way to improve the damaged hair is to apply a vegetable oil such as a camellia oil and olive oil to hair to replenish a moderate amount of oil so as to impart smoothness and flexibility to hair. Furthermore, in order to improve feeling in use, these vegetable oils have been tried to be used in combination with a compound such as high molecular weight silicone, dimethicone, and volatile silicone.

For example, Patent Literature 1 discloses a hair cosmetic comprising (A) a hydrocarbon having a dynamic viscosity of 2.0-36.0 $mm^2s^{-1}$ at 40° C., (B) an amino-modified silicone, (C) a compound having a polyoxyethylene group and a polyoxypropylene group, and (D) a vegetable oil selected from olive oil, grape seed oil, jojoba oil and camellia oil. The component (C) is a compound of the general formula: $R^1O—[(C_2H_4O)_p(C_3H_6O)_q]—R^2$ (wherein $R^1$ and $R^2$ independently denote a hydrogen atom, an alkyl group, or a glyceryl group, and p and q are independently an integer: p=2 to 70, q=2 to 70). The hair cosmetic alleviates stiffness of the damaged hair which is prone to expand due to its stiffness, thus suppressing the expansion of the hair to improve hair manageability, and also reduces stickiness.

Patent Literature 2 discloses a hair cosmetic comprising (A) 1 to 15% by mass of a vegetable oil, (B) a volatile oil, (C) a high molecular weight dimethylpolysiloxane, and (D) a dimethylpolysiloxane having a hydroxyl group, a polyoxyethylene group and/or a polyoxypropylene group. The hair cosmetic is primarily composed of dimethylpolysiloxane. The hair cosmetic imparts conflicting feels to hair: excellent gloss and a smooth and moist touch as well as a dry feel at the same time.

Patent Literature 3 discloses a hair cosmetic comprising (A) a polymer silicone, (B) a volatile hydrocarbon oil, (C) a cholesterol derivative, (D) a low viscosity silicone oil. The hair cosmetic, which exhibits excellent spreadability, smoothness and flexibility when applied to hair, is not sticky to the hair, and can impart a smooth and flexible feel to hair and proper hair manageability after application.

Patent Literature 4 discloses a hair cosmetic comprising predetermined amounts of (A) a hydroxy ether amine compound, (B) a higher alcohol and/or a higher fatty acid, (C) an inorganic acid and/or organic acid, (D) a dimethyl polysiloxane and/or silicone derivative, and (E) an aromatic alcohol, the hair cosmetic having a pH of 2.0 to 7.0. The hair cosmetic exhibits hair-conditioning effect satisfying desirable properties such as smoothness, finger-combability, dry feeling and moistness on both of damaged hair and non-damaged hair from the start of the use to the time after use.

Hair cosmetics composed of only plant oils cause uncomfortable sticky feeling when applied on hair, giving a heavy finish, and thus is unsatisfactory. Accordingly, it has been attempted to use silicone oil as described in Patent Literatures 1 to 4. Thus, the use of silicone oil can impart a refreshing feel, resulting in a lighter finish, but it is not sufficient for improving the feeling in user. Furthermore, these hair cosmetics do not contain an ester composed of dipentaerythritol and at least one fatty acid selected from the group consisting of fatty acids having 5 to 16 carbon atoms. Furthermore, no description is found that suggests the use of the ester compound.

Patent Literature 5 discloses a liquid ester composition obtained by esterifying a branched isostearic acid represented by the chemical formula: $R—C(COOH)H—(CH_2CH_2)—R$ (wherein R denotes a branched hydrocarbon having seven carbon atoms) with dipentaerythritol, the liquid ester composition having a viscosity of 100,000 to 2,000,000 mPa·s at 25° C.; a hydroxyl value of 10 to 160; and a cloud point of less than 5° C. The liquid ester composition is prepared through a reaction of dipentaerythritol with a specifically branched stearic acid having 18 carbons. An excellent long-lasting cosmetic film of the liquid ester composition provide not only gloss and a moisture feel comparable to a film of a composition containing polybutene, which has been usually incorporated in cosmetic compositions, but also pigment dispersibility and hydrating ability that the polybutene composition cannot provide.

Patent Literature 6 discloses an oil-based cosmetic comprising (A) a liquid ester composition obtained by esterifying a branched isostearic acid represented by the general formula: $R^1—C(COOH)H—CH_2CH_2—R^2$ (wherein $R^1$ and $R^2$ denote a branched hydrocarbon having seven carbon atoms and may be the same or different), and (B) a silicone resin. The component (A) is an isostearic acid having eighteen carbon atoms, and includes dipentaerythritol pentaisostearate, dipentaerythritol tetraisostearate, dipentaerythritol triisostearate, glyceryl triisostearate, and diglyceryl triisostearate. The component (B) includes trimethylsiloxy silicic acid, perfluoroalkyl-polyalkylsiloxy silicic acid. The invention described in Patent Literature 6 provides an oil-based cosmetic which is excellent in the feel at the time of application, gloss, retention of a moisture feel, and retention of cosmetic effects. The oil-based cosmetic is preferably used as a cosmetic for lip.

CITATION LIST

Patent Literature

Patent Literature 1: Japanese Patent Application Laid-Open 2009-51817
Patent Literature 2: Japanese Patent Application Laid-Open 2009-221143
Patent Literature 3: Japanese Patent Application Laid-Open 2007-223930
Patent Literature 4: Japanese Patent Application Laid-Open 2007-161605
Patent Literature 5: WO2006/003992
Patent Literature 6: Japanese Patent Application Laid-Open 2006-111543

SUMMARY OF INVENTION

Technical Problem

The present invention provides a damaged hair improving agent which agent imparts a sleek feel to the damaged hair and reduces gritty feel of the damaged hair to impart smooth feel the damaged hair, and a process for improving the damaged hair using the same.

Solution to Problem

The present inventors have attempted a variety of investigations to solve the problems described above. As a result, the present inventors have found that an application of a composition comprising a component (A) compounded with one or more substances selected from the group consisting of components (B), (C), and (D) to hair can solve the problems described above, and thus have completed the present invention.

The present invention provides:

(1) A damaged hair improving agent comprising: (A) an ester compound made from dipentaerythritol and at least one fatty acid selected from the group consisting of fatty acids having 5 to 16 carbon atoms, wherein the molar ratio of the dipentaerythritol residue to the fatty acid residue ranges from 1.0:3.0 to 1.0:6.0, and one or more substances selected from the group consisting of (B) an ester compound having a linear or branched alkyl or alkenyl group having 16 to 18 carbon atoms wherein hydrogen atoms on these groups are optionally replaced with hydroxyl groups, and a viscosity of 2,000 mPa·s or less at 25° C. (exclusive of the component (A)), (C) an alcohol having a linear or branched alkyl or alkenyl group having 16 to 18 carbon atoms and a viscosity of 2,000 mPa·s or less at 25° C., and (D) hydrocarbon oil having at least 20 carbon atoms.

Preferred embodiments provide:

(2) The damaged hair improving agent according to item (1), comprising at least one substance selected from the group consisting of the component (B), the component (C), and the component (D), in an amount of 10 to 1,200 parts by mass in total of the components of (B), (C) and (D) relative to 100 parts by mass of the component (A);

(3) The damaged hair improving agent according to item (1), comprising at least one substance selected from the group consisting of the component (B), the component (C), and the component (D), in an amount of 10 to 1,000 parts by mass in total of the components of (B), (C) and (D) relative to 100 parts by mass of the component (A);

(4) The damaged hair improving agent according to item (1), comprising at least one substance selected from the group consisting of the component (B), the component (C), and the component (D), in an amount of 10 to 150 parts by mass in total of the components of (B), (C) and (D) relative to 100 parts by mass of the component (A);

(5) The damaged hair improving agent according to item (1), comprising at least one substance selected from the group consisting of the component (B), the component (C), and the component (D), in an amount of 20 to 100 parts by mass in total of the components of (B), (C) and (D) relative to 100 parts by mass of the component (A);

(6) The damaged hair improving agent according to any one of items (1) to (5), wherein the molar ratio of the dipentaerythritol residue to the fatty acid residue having 5 to 16 carbon atoms in the component (A) ranges from 1.0:3.5 to 1.0:6.0;

(7) The damaged hair improving agent according to any one of items (1) to (5), wherein the molar ratio of the dipentaerythritol residue to the fatty acid residue having 5 to 16 carbon atoms in the component (A) ranges from 1.0:4.0 to 1.0:6.0;

(8) The damaged hair improving agent according to any one of items (1) to (7), wherein the fatty acid in the component (A) has 8 to 16 carbon atoms;

(9) The damaged hair improving agent according to any one of items (1) to (7), wherein the fatty acid in the component (A) has 9 to 16 carbon atoms;

(10) The damaged hair improving agent according to any one of items (1) to (9), wherein the fatty acid in the component (A) is selected from the group consisting of isononanoic acid, neopentanoic acid, 2-ethylhexanoic acid, isomyristic acid, and isopalmitic acid;

(11) The damaged hair improving agent according to any one of items (1) to (9), wherein the fatty acid in the component (A) is isononanoic acid;

(12) The damaged hair improving agent according to any one of items (1) to (11), wherein the component (B) is selected from the group consisting of isostearyl neopentanoate, polyglyceryl-2 triisostearate, triisostearin, cetyl ethylhexanoate, polyglyceryl-2 tetraisostearate, oleyl erucate, isostearyl isostearate, pentaerythrityl tetraisostearate, dipentaerythritol hexaisostearate, hexyldecylisostearate, and ethylhexyl hydroxystearate;

(13) The damaged hair improving agent according to any one of items (1) to (12), wherein the component (C) is isostearyl alcohol; and

(14) The damaged hair improving agent according to any one of items (1) to (13), wherein the component (D) is selected from the group of squalane and mineral oil.

The present invention also provides:

(15) A process for improving damaged hair by applying a composition to hair, the composition comprising (A) an ester compound made from dipentaerythritol and at least one fatty acid selected from the group consisting of fatty acids having 5 to 16 carbon atoms, wherein the molar ratio of the dipentaerythritol residue to the fatty acid residue ranges from 1.0:3.0 to 1.0:6.0, and one or more substances selected from the group consisting of (B) an ester compound having a linear or branched alkyl or alkenyl group having 16 to 18 carbon atoms wherein hydrogen atoms on these groups are optionally replaced with hydroxyl groups, and a viscosity of 2,000 mPa·s or less at 25° C. (exclusive of the component (A)), (C) an alcohol having a linear or branched alkyl or alkenyl group having 16 to 18 carbon atoms and a viscosity of 2,000 mPa·s or less at 25° C., and (D) hydrocarbon oil having at least 20 carbon atoms.

Preferred embodiments include:

(16) The process for improving damaged hair according to item (15), wherein the composition comprises at least one substance selected from the group consisting of the component (B), the component (C), and the component (D), in an amount of 10 to 1,200 parts by mass in total of the components of (B), (C) and (D) relative to 100 parts by mass of the component (A);

(17) The process for improving damaged hair according to item (15), wherein the composition comprises at least one substance selected from the group consisting of the component (B), the component (C), and the component (D), in an amount of 10 to 1,000 parts by mass in total of the components of (B), (C) and (D) relative to 100 parts by mass of the component (A);

(18) The process for improving damaged hair according to item (15), wherein the composition comprises at least one substance selected from the group consisting of the component (B), the component (C), and the component (D), in an amount of 10 to 150 parts by mass in total of the components of (B), (C) and (D) relative to 100 parts by mass of the component (A);

(19) The process for improving damaged hair according to item (15), wherein the composition comprises at least one substance selected from the group consisting of the component (B), the component (C), and the component (D), in an amount of 20 to 100 parts by mass in total of the components of (B), (C) and (D) relative to 100 parts by mass of the component (A);

(20) The process for improving damaged hair according to any one of items (15) to (19), wherein the molar ratio of the dipentaerythritol residue to the fatty acid residue having 5 to 16 carbon atoms in the component (A) ranges from 1.0:3.5 to 1.0:6.0;

(21) The process for improving damaged hair according to any one of items (15) to (19), wherein the molar ratio of the dipentaerythritol residue to the fatty acid residue having 5 to 16 carbon atoms in the component (A) ranges from 1.0:4.0 to 1.0:6.0;

(22) The process for improving damaged hair according to any one of items (15) to (21), wherein the fatty acid of the component (A) has 8 to 16 carbon atoms;

(23) The process for improving damaged hair according to any one of items (15) to (21), wherein the fatty acid of the component (A) has 9 to 16 carbon atoms;

(24) The process for improving damaged hair according to any one of items (15) to (23), wherein the fatty acid in the component (A) is selected from the group consisting of isononanoic acid, neopentanoic acid, 2-ethylhexanoic acid, isomyristic acid, and isopalmitic acid;

(25) The process for improving damaged hair according to any one of items (15) to (23), wherein the fatty acid in the component (A) is isononanoic acid;

(26) The process for improving damaged hair according to any one of items (15) to (25), wherein the component (B) is selected from the group consisting of isostearyl neopentanoate, polyglyceryl-2 triisostearate, triisostearin, cetyl ethylhexanoate, polyglyceryl-2 tetraisostearate, oleyl erucate, isostearyl isostearate, pentaerythrityl tetraisostearate, dipentaerythrityl hexaisostearate, hexyldecylisostearate, and ethylhexyl hydroxystearate;

(27) The process for improving damaged hair according to any one of items (15) to (26), wherein the component (C) is isostearyl alcohol;

(28) The process for improving damaged hair according to any one of items (15) to (27), wherein the component (D) is selected from the group of squalane and mineral oil.

Advantageous Effects of Invention

A damaged hair improving agent and a process for improving damaged hair using the same of the present invention imparts a sleek feel to the damaged hair and reduces gritty feel of the damaged hair to impart smooth feel. In addition to the above effects, they provide not only moderate emollient and moisture-retaining properties but also gloss-retaining property, smooth sensation, adhesiveness, durability of cosmetic effect, storage stability and safety to the skin.

DESCRIPTION OF EMBODIMENTS

In the damaged hair improving agent of the present invention, the component (A), ester compound, is made from a dipentaerythritol and at least one fatty acid selected from the group consisting of fatty acids having 5 to 16 carbon atoms, preferably having 8 to 16 carbon atoms, more preferably having 9 to 16 carbon atoms. The fatty acid may be either linear or branched and either saturated or unsaturated. Examples include n-pentanoic acid, neopentanoic acid, n-hexanoic acid, isohexanoic acid, octanoic acid, isononanoic acid, nonanoic acid, 2-ethylhexanoic acid, neodecanoic acid, isomyristic acid, and isopalmitic acid, preferably isononanoic acid, neopentanoic acid, 2-ethylhexanoic acid, neodecanoic acid, isomyristic acid, isopalmitic acid, and more preferably isononanoic acid.

The molar ratio of the dipentaerythritol residue to the fatty acid residue in the component (A) ester compound ranges from 1.0:3.0 to 1.0:6.0, preferably from 1.0:3.5 to 1.0:6.0, more preferably from 1.0:4.0 to 1.0:6.0. A molar equivalent ratio of the fatty acid to dipentaerythritol of less than 3.0 at the time of manufacture of the ester compound to attain a ratio of the fatty acid residues less than the above-mentioned lower limit may cause insufficient reaction of dipentaerythritol, thus resulting in a significant amount of unnecessary unreacted dipentaerythritol which remains in the ester-containing reaction products. Consequently, the application of the entire reaction products for the damaged hair improving agent will prevent the component (A) ester compound from sufficiently exerting the effects of the present invention. This behavior becomes pronounced with a decrease in the molar equivalent ratio of the fatty acid to dipentaerythritol at the time of manufacture. Accordingly, at a molar equivalent ratio of the fatty acid to dipentaerythritol not more than about 2.0, excess dipentaerythritol substantially precludes formation of the ester compound.

The component (A), an ester compound, consisting of dipentaerythritol and the fatty acid includes monoester, diester, triester, tetraester, pentaester, and hexaester of dipentaerythritol and the fatty acid. The ester compound used in the present invention contains one or more, preferably two or more ester compounds consisting of dipentaerythritol and the fatty acid having 5 to 16 carbon atoms.

The component (A), ester compound, used in the damaged hair improving agent can further contain substances formed as byproducts at the time of manufacture and unreacted substances in addition to the above ester compounds. Although the substances formed as byproducts are not known in detail, they are probably substances derived from raw materials, acid anhydrides, self-condensation products of dipentaerythritol, and polyesters. The content of such substances will vary depending on several factors such as the molar equivalent ratio of dipentaerythritol to the fatty acid having 5 to 16 carbon atoms and the type of the fatty acid, and is preferably 2.0% or less by mass relative to the total of the ester compounds and byproducts thereof. The component (A), ester compound, used in the present invention can be used without separating the byproducts, and thus has an advantage in that such an operation as separation can be omitted. Obviously, the ester compound may also be used after removal of the byproducts.

With the hydroxyl value of the component (A), ester compound, the upper limit of is preferably 340, more preferably 200, and still more preferably 150, while the lower limit is not restricted, but preferably 0.5. A value exceeding the upper limit leads to a decrease in compatibility of the component (A) with oil bases such as the component (B), the component (C), and the component (D), whereas a value below the lower limit leads to poor moisture-retaining property or emollient property of the component (A).

With the saponification value of the component (A), ester compound, the upper limit is preferably 450, more preferably 360, and still more preferably 320, while the lower limit is preferably 170, more preferably 175, and still more preferably 180. A value exceeding the upper limit leads to low adhesion to hair, whereas a value below the lower limit leads to an unpleasant sticky feeling when the composition is applied to hair, which is unfavorable for repairing hair damage.

With the viscosity (25° C.) of the component (A), ester compound, the upper limit is preferably 40,000 mPa·s, more preferably 24,000 mPa·s, still more preferably 20,000 mPa·s, while the lower limit is preferably 500 mPa·s. A viscosity exceeding the upper limit causes high stickiness, resulting in an unpleasant sticky feeling when the composition is applied to hair, whereas a viscosity below the lower limit leads to low adhesion to hair, which is unfavorable for a damaged hair improving agent. The viscosity is determined with a Brookfield viscosimeter: DV-II+ (spindle No. 3, 12 rpm, 25° C.).

The component (A), ester compound, can be prepared by a reaction of dipentaerythritol with at least one fatty acid selected from the group consisting of fatty acids having 5 to 16, preferably 8 to 16, more preferably 9 to 16 carbon atoms in a molar equivalent ratio of dipentaerythritol to the fatty acid of 1.0:3.0 to 1.0:6.0, preferably 1.0:3.5 to 1.0:6.0, and more preferably 1.0:4.0 to 1.0:6.0. The examples of the fatty acid include those described above. A molar equivalent ratio of the fatty acid to the dipentaerythritol of less than 3.0 causes insufficient reaction of dipentaerythritol, as described above, thus resulting in a significant amount of unnecessary unreacted dipentaerythritol which remains in the ester-containing reaction product. Consequently, the use of the entire reaction product will prevent the ester compound from sufficiently exerting the effects of the present invention. This behavior becomes pronounced with a decrease in molar equivalent ratio of the fatty acid to dipentaerythritol in the manufacturing process; thus, at a molar equivalent ratio of about 2.0 or less, excess dipentaerythritol substantially precludes the formation of the ester compound. By contrast, an excess amount of the fatty acid to dipentaerythritol can be fed in the reaction system. Since unreacted fatty acids remaining in the product sometimes impair the quality of the ester compound, the unreacted fatty acids should preferably be removed after the reaction. The reaction of dipentaerythritol with the fatty acids can be conducted by any process known in the art.

In the damaged hair improving agent of the present invention, the component (B), ester compound, has a linear or branched alkyl or alkenyl group having 16 to 18 carbon atoms and a viscosity of 2,000 mPa·s or less at 25° C. However, the component (B), ester compound, does not include the component (A), ester compound. The component (B), ester compound, preferably has a linear or branched alkyl or alkenyl group having 18 carbon atoms. Furthermore, the hydrogen atoms on the linear or branched alkyl or alkenyl group having 16 to 18 carbon atoms may optionally be replaced with hydroxyl groups. Preferably, one or two hydrogen atoms on these groups are replaced by hydroxyl groups. The lower limit of the viscosity is preferably 10 mPa·s. at 25° C. A viscosity exceeding the upper limit leads to high stickiness, resulting in an unpleasant sticky feeling when the composition is applied to hair, whereas a viscosity below the lower limit leads to low adhesion to hair, which is unfavorable for a damaged hair improving agent. The viscosity was determined with a Brookfield viscosimeter: DV-II+(spindle No. 3, 12 rpm, 25° C.). Examples of the component (B), ester compound, include preferably isostearyl neopentanoate, polyglyceryl-2 triisostearate, triisostearin, cetyl ethylhexanoate, polyglyceryl-2 tetraisostearate, oleyl erucate, isostearyl isostearate, pentaerythrityl tetraisostearate, dipentaerythrityl hexaisostearate, hexyldecyl isostearate, and ethylhexyl hydroxystearate.

In the damaged hair improving agent of the present invention, the component (C), alcohol, has a linear or branched alkyl or alkenyl group having 16 to 18 carbon atoms and a viscosity of 2,000 mPa·s or less at 25° C. The component (C), alcohol, preferably has a linear or branched alkyl or alkenyl group having 18 carbon atoms. The lower limit of viscosity is preferably 10 mPa·s at 25° C. A viscosity exceeding the upper limit causes stronger stickiness, resulting in an unpleasant sticky feeling when the composition is applied to hair, and a viscosity below the lower limit decreases the adhesion to hair, which is unfavorable for a damaged hair improving agent. The above viscosity was determined with a Brookfield viscosimeter: DV-II+(spindle No. 3, 12 rpm, 25° C.). The preferred examples of component (C), alcohol, include isostearyl alcohol.

In the damaged hair improving agent of the present invention, the component (D), hydrocarbon oil, has at least 20 carbon atoms, preferably 20 to 40 carbon atoms. The number of carbon atoms below the lower limit causes low adhesion to hair, which is unfavorable for a damaged hair improving agent, whereas the number of carbon atoms above the upper limit causes high stickiness, resulting in an unpleasant sticky feeling when the composition is applied to hair. Preferred examples of the component (C), hydrocarbon oil, include squalane and mineral oil.

In the damaged hair improving agent of the present invention, the upper limit of the total amount of the components (B), (C), and (D) relative to 100 parts by mass of the component (A) is preferably 1,200 parts by mass, more preferably 1,000 parts by mass, still more preferably 300 parts by mass, even still more preferably 150 parts by mass, and most preferably 100 parts by mass, while the lower limit thereof is preferably 10 parts by mass, more preferably 20 parts by mass, still more preferably 30 parts by mass. The total content of the components (A), (B), (C), and (D) in the damaged hair improving agent is in the range of preferably 0.1 to 50% by mass, more preferably 0.5 to 40% by mass, still more preferably 0.5 to 30% by mass, and most preferably 0.5 to 10% by mass.

The damaged hair improving agent of the present invention containing the component (A) and one or more substances selected from the group consisting of the components (B), (C), and (D) can be used in hair care cosmetics such as shampoos, hair treatments, hair waxes and hair oils. The content of the damaged hair improving agent of the present invention in the hair care cosmetics is preferably 0.1 to 50% by mass, more preferably 0.5 to 40% by mass, and still more preferably 0.5 to 30% by mass. Furthermore, each of the hair care cosmetics can be prepared by any process known in the art.

The process for improving damaged hair of the present invention can be performed by applying a composition containing the component (A) and one or more substances selected from the group consisting of the components (B), (C), and (D) to hair. The damaged hair improving agent is preferably applied in the form of hair care cosmetics containing the composition, such as shampoos, hair treatments, hair waxes, and hair oils. The application to hair can be performed according to a conventional manner.

The present invention will be described in more detail by way of examples, but should not be limited to these examples.

EXAMPLES

<Component (A)>

Component (A) and Comparative component (A) were synthesized in accordance with the following Synthesis Examples (synthesis of component (A)) and Comparative Synthesis Examples.

Synthesis Examples and Comparative Synthesis Examples

The substances used in the following Synthesis Examples and Comparative Synthesis Examples were as follows, unless otherwise stated:

Dipentaerythritol: "Dipentaerythritol" (trade mark) from Koei Chemical Co., Ltd., Isononanoic acid $(C(CH_3)_3CH_2CH(CH_3)CH_2COOH)$: "KYOWANOIC-N" (trade mark) from Kyowa Hakko Chemical Co., Ltd., Neopentanoic acid $((CH_3)_3CCOOH)$: Neopentanioc acid (trade mark) from Exxon Mobil Corporation, 2-Ethylbhexanoic acid $(CH_3(CH_2)_3CH(CH_2CH_3)COOH)$: Octyl acid (trade mark) from Kyowa Hakko Chemical Co., Ltd., Neodecanoic acid $(C_9H_{19}COOH$: a mixture of structural isomers): Neodecanoic acid (trade mark) from Exxon Mobil Corporation, Isomyristic acid (a mixture of $CH_3CH(CH_3)(CH_2)_4CH[CH_3CH(CH_3)CH_2CH_2]COOH$ and $CH_3(CH_2)_2CH(CH_3)(CH_2)_2CH[CH_3(CH_2)_2CH(CH_3)]COOH)$: Isomyristic acid (trade mark) from Nissan Chemical Industries, Ltd., Isopalmitic acid $(CH_3(CH_2)_7CH(C_6H_{13})COOH$: Isopalmitic acid (trade mark) from Nissan Chemical Industries, Ltd., Isobutanoic acid (isobutyric acid) $((CH_3)_2CHCOOH)$: Isobutyric acid (trade mark) from OXEA Corporation Isostearic acid $(C_{17}H_{35}COOH$, a mixture of structural isomers): "Isostearic acid EX" (trade mark) from Kokyu Alcohol Kogyo Co., Ltd.

The acid value, hydroxyl value, saponificaion value, viscosity, adhesive property, and gloss property of the dipentaerythritol fatty acid esters in the Synthesis Examples and Comparative Synthesis Examples were determined as follows.

Acid value: determined in accordance with "the Japanese Standards of Cosmetic Ingredients, 18 Method for the Determination of Acid Value".

Hydroxyl value: determined in accordance with "the Japanese Standards of Cosmetic Ingredients, 24 Method for the Determination of Hydroxyl Value".

Saponificaion value: determined in accordance with "the the Japanese Standards of Cosmetic Ingredients, 16 Method for the Saponificaion Value".

Viscosity: determined by Brookfield Viscometer DV-II+ (Spindle No. 3, 12 rpm, 25° C.).

Synthesis Example 1

A 3,000 mL four neck flask equipped with a stirrer, thermometer, a nitrogen gas inlet tube, a Dean Stark apparatus and a condenser was charged with dipentaerythritol (381.5 g, 1.5 mol), isononanoic acid (number of carbon atoms: 9, 948 g, 6.0 mol), toluene (150 mL) as a solvent, and p-toluenesulfonic acid (4.0 g) as a catalyst. The mixture was then heated to 200° C. under a nitrogen gas stream at a rate of 20 mL/min. The reaction was carried out under reflux at the temperature while distilling off the produced water with the solvent azeotropically. When the distillation-off of the produced water subsided, the temperature was raised to 220° C. to further continue the reaction. When the distillation-off of the water stopped, the reaction was terminated. It took about 20 hours from the start of the reaction to this point. After the temperature was lowered to 180° C., the pressure was reduced to about 20 mmHg to remove toluene (solvent), completely. The resulting reaction product was subjected to conventional purification treatment for decolorization and deodorization. Dipentaerythritol fatty acid ester was obtained as pale yellow viscous oil in an amount of 952.3 g (acid value: 0.65, hydroxyl value: 125, saponification value: 277.7).

The molar equivalent ratio between dipentaerythritol and isononanoic acid used in the reaction was 1.0:4.0.

Potassium hydroxide in ethanol solution was added to the resulting dipentaerythritol fatty acid ester to hydrolyze it. The hydrolyzed reaction mixture was then filtered and the unsaponified product was removed. Ethanol was removed from the filtrate which was then acidified with hydrochloric acid, from which the saponified product was extracted with hexane. The unsaponified and saponified products each were silylated and methylated according to conventional methods, and subsequently the products were analyzed for identification and determination by gas chromatography (6890N from Agilent Technologies, Inc). The results showed that the resulting dipentaerythritol fatty acid ester was composed of dipentaerythritol and isononanoic acid, and the molar ratio of the dipentaerythritol residue to the isononanoic acid residue was 1.0:4.0.

Synthesis Example 2

The process of Synthesis Example 1 was performed except that the amount of isononanoic acid used was changed to 1422 g (9.0 mol). Dipentaerythritol fatty acid ester was obtained as pale yellow viscous oil in an amount of 1392 g (acid value: 0.02, hydroxyl value: 1.1, saponification value: 303.5).

The molar equivalent ratio between dipentaerythritol and isononanoic acid used in the reaction was 1.0:6.0.

Synthesis Example 3

The process of Synthesis Example 1 was performed except that the amount of isononanoic acid used was changed to 711 g (4.5 mol). Dipentaerythritol fatty acid ester was obtained as pale yellow viscous oil in an amount of 802 g (acid value: 0.43, hydroxyl value: 226.1, saponification value: 256.4).

The molar equivalent ratio between dipentaerythritol and isononanoic acid used in the reaction was 1.0:3.0.

Synthesis Example 4

The process of Synthesis Example 1 was performed except that neopentanoic acid (5 carbon atoms) (612.8 g, 6.0 mol) was used in place of isononanoic acid. Dipentaerythritol fatty acid ester was obtained as pale yellow viscous oil in an amount of 815 g (acid value: 0.26, hydroxyl value: 171.3, saponification value: 376.2).

The molar equivalent ratio between dipentaerythritol and neopentanoic acid used in the reaction was 1.0:4.0.

Synthesis Example 5

The process of Synthesis Example 1 was performed except that 2-ethylhexanoic acid (8 carbon atoms) (865.3 g, 6.0 mol) was used in place of isononanoic acid. Dipentaerythritol fatty acid ester was obtained as pale yellow viscous oil in an amount of 1034 g (acid value: 0.48, hydroxyl value: 133.8, saponification value: 298.3).

The molar equivalent ratio between dipentaerythritol and 2-ethylhexanoic acid used in the reaction was 1.0:4.0.

Synthesis Example 6

The process of Synthesis Example 1 was performed except that neodecanoic acid (10 carbon atoms) (1033.6 g, 6.0 mol) was used in place of isononanoic acid. Dipentaerythritol fatty acid ester was obtained as pale yellow viscous oil in an amount of 1032.5 g (acid value: 0.39, hydroxyl value: 116.6, saponification value: 259.8).

The molar equivalent ratio between dipentaerythritol and neodecanoic acid used in the reaction was 1.0:4.0.

Synthesis Example 7

The process of Synthesis Example 1 was performed except that 2-isomyristic acid (14 carbon atoms) (1370 g, 6.0 mol) was used in place of isononanoic acid. Dipentaerythritol fatty acid ester was obtained as pale yellow viscous oil in an amount of 1347.9 g (acid value: 0.67, hydroxyl value: 93.1, saponification value: 204.2).

The molar equivalent ratio between dipentaerythritol and isomyristic acid used in the reaction was 1.0:4.0.

Synthesis Example 8

The process of Synthesis Example 1 was performed except that isopalmitic acid (16 carbon atoms) (1539 g, 6.0 mol) was used in place of isononanoic acid. Dipentaerythritol fatty acid ester was obtained as pale yellow viscous oil in an amount of 1431.9 g (acid value: 0.92, hydroxyl value: 79.0, saponification value: 182.4).

The molar equivalent ratio between dipentaerythritol and isopalmitic acid used in the reaction was 1.0:4.0.

Comparative Synthesis Example 1

The process of Synthesis Example 1 was performed except that the amount of isononanoic acid used was changed to 474 g (3.0 mol). Dipentaerythritol fatty acid ester, however, was not obtained as a large amount of unreacted dipentaerythritol remained.

The molar equivalent ratio between dipentaerythritol and isononanoic acid used in the reaction was 1.0:2.0.

Comparative Synthesis Example 2

The process of Synthesis Example 1 was performed except that isobutanoic acid (isobutyric acid) (4 carbon atoms) (528.7 g, 6.0 mol) was used in place of isononanoic acid. Dipentaerythritol fatty acid ester was obtained as pale yellow viscous oil in an amount of 665.8 g (acid value: 0.15, hydroxyl value: 189.1, saponification value: 420.3).

The molar equivalent ratio between dipentaerythritol and isobutanoic acid (isobutyric acid) used in the reaction was 1.0:4.0.

Comparative Synthesis Example 3

The process of Synthesis Example 1 was performed except that isostearic acid (18 carbon atoms) (1740 g, 6.0 mol) was used in place of isononanoic acid. Dipentaerythritol fatty acid ester was obtained as pale yellow viscous oil in an amount of 1671.2 g (acid value: 0.05, hydroxyl value: 74.5, saponification value: 169.7).

The molar equivalent ratio between dipentaerythritol and isostearic acid used in the reaction was 1.0:4.0.

Properties of each substance obtained in the Synthesis Examples and the Comparative Synthesis Examples are shown in Table 1.

[Table. 1]

TABLE 1

| | Molar equivalent ratio in the reaction | | | | | Viscosity | | Gloss | |
|---|---|---|---|---|---|---|---|---|---|
| | Dipenta-erythritol | Fatty acid | Type of fatty acid | Acid Value | Hydroxyl value | Saponification value | (mPa · s, 25° C.) | Adhesion | Oil base alone | Contact with water |
| Syn. Ex. 1 | 1.0 | 4.0 | Isononanoic acid | 0.65 | 125 | 277.7 | 15,550 | G | 78 | 96 |
| Syn. Ex. 2 | 1.0 | 6.0 | Isononanoic acid | 0.02 | 1.1 | 303.5 | 1,200 | G | 73 | 97 |
| Syn. Ex. 3 | 1.0 | 3.0 | Isononanoic acid | 0.43 | 226.1 | 256.4 | 25,000 | G | 74 | 92 |
| Syn. Ex. 4 | 1.0 | 4.0 | Neopentanoic acid | 0.26 | 171.3 | 376.2 | 19,400 | G | 74 | 91 |
| Syn. Ex. 5 | 1.0 | 4.0 | 2-Ethylhexanoic acid | 0.48 | 133.8 | 298.3 | 16,200 | G | 73 | 90 |
| Syn. Ex. 6 | 1.0 | 4.0 | Neodecanoic acid | 0.39 | 116.2 | 259.8 | 12600 | G | 73 | 91 |
| Syn. Ex. 7 | 1.0 | 4.0 | Isomyristic acid | 0.67 | 93.1 | 204.2 | 2400 | G | 73 | 90 |
| Syn. Ex. 8 | 1.0 | 4.0 | Isopalmitic acid | 0.92 | 79 | 182.4 | 600 | G | 73 | 90 |
| Comp. Syn. Ex. 1 | 1.0 | 2.0 | Isononanoic acid | —[1] | —[1] | —[1] | —[1] | —[1] | —[1] | —[1] |
| Comp. Syn. Ex. 2 | 1.0 | 4.0 | Isobutyric acid | 0.15 | 189.1 | 420.3 | 22,800 | B | 73 | 90 |
| Comp. Syn. Ex. 3 | 1.0 | 4.0 | Isostearic acid | 0.05 | 74.5 | 169.7 | 1,900 | M | 74 | 36 |

In Table 1,
[1]Dipentaerythritol fatty acid ester was not obtained as a large amount of unreacted dipentaerythritol remained.

In Table 1,
[1] Dipentaerythritol fatty acid ester was not obtained as a large amount of unreacted dipentaerythritol remained.

In Synthesis Examples 1 to 3, the molar equivalent ratio of isononanoic acid (9 carbon atoms) was varied within the range of the present invention. The viscosity of the resulting dipentaerythritol fatty acid ester of Synthesis Example 2 was significantly low. Synthesis Examples 4, 5, 6, 7 and 8 used neopentanoic acid (5 carbon atoms), 2-ethylhexanoic acid (8 carbon atoms), neodecanoic acid (10 carbon atoms), isomyristic acid (14 carbon atoms), and isopalmitic acid (16 carbon atoms), respectively, in place of isononanoic acid in Synthesis Example 1. The resulting dipentaerythritol fatty acid ester had a tendency to decrease in viscosity with an increasing number of carbon atoms of the fatty acid.

In Comparative Synthesis Example 1, Synthesis Example 1 was performed except that the molar equivalent ratio of isononanoic acid is below the range of the present invention. Dipentaerythritol fatty acid ester was not obtained as a large amount of unreacted dipentaerythritol remained. Comparison Examples 2 and 3 used isobutanoic acid (isobutyric acid) (4 carbon atoms) and isostearic acid (18 carbon atoms), which are fatty acids having the number of carbon atoms out of the range of the present invention, respectively in place of isononanoic acid in Synthesis Example 1. The viscosity of the dipentaerythritol fatty acid ester obtained in Comparative Synthesis Example 2 was high, whereas the viscosity of the dipentaerythritol fatty acid ester obtained in Comparative Synthesis Example 3 was also rather higher compared with the dipentaerythritol fatty acid ester obtained in Synthesis Example 8.

Examples and Comparative Examples

The substances used in Examples and Comparative Examples are as follows, unless otherwise stated:
<Component (B)>
Isostearyl neopentanoate: NEOLIGHT 180P (trade mark) from Kokyu Alcohol Kogyo Co., Ltd.
Polyglyceryl-2 triisostearate: RISOREX PGIS23 (trade mark) from Kokyu Alcohol Kogyo Co., Ltd.
Triisostearin: TISG (trade mark) from Kokyu Alcohol Kogyo Co., Ltd.
Dipentaerythrityl hexaisostearate: HAILUCENT DPIS6 (trade mark) from Kokyu Alcohol Kogyo Co., Ltd., which is composed of mainly (about 80%) isostearic acid having a methyl-branched structure at any of the 14- to 16-positions, and the rest is a mixture of fatty acid having 16 or less and fatty acid having 18 or more carbon atoms.
Cetyl ethylhexanoate: CEH (trade mark) from Kokyu Alcohol Kogyo Co., Ltd.
Polyglyceryl-2 tetraisostearate: RISOREX PGIS24 (trade mark) from Kokyu Alcohol Kogyo Co., Ltd.
Oleyl erucate: CETIOL J600 (trade mark) from Cognis Corp.
Isostearyl isostearate: ISIS (trade mark) from Kokyu Alcohol Kogyo Co., Ltd.
Pentaerythrityl tetraisostearate: KAK PTI (trade mark) from Kokyu Alcohol Kogyo Co., Ltd.
Hexyldecyl isostearate: ICIS (trade mark) from Kokyu Alcohol Kogyo Co., Ltd.
Ethylhexyl hydroxystearate: RISOCAST IOHS (trade mark) from Kokyu Alcohol Kogyo Co., Ltd.
<Component (C)>
Isostearyl alcohol: ISOSTEARYL ALCOHOL EX (trade mark) from Kokyu Alcohol Kogyo Co., Ltd.
<Component (D)>
Squalane: OLIVE SQUALANE (trade mark) from Kokyu Alcohol Kogyo Co., Ltd.
Mineral oil: HICALL K-230 (trade mark) from Kaneda Co., Ltd.
<Other Components>
Triethylhexanoin: TOG (trade mark) from Kokyu Alcohol Kogyo Co., Ltd.
Polyquaternium-10: Catinal HC-100 (trade mark) from Toho Chemical Industry Co., Ltd.
Polyglyceryl-10 isostearate: S-FACE IS-1001P (trade mark) from Sakamoto Yakuhin Kogyo Co., Ltd.
Polyglyceryl-10 laurate: RISOREX PGL101 (trade mark) from Kokyu Alcohol Kogyo Co., Ltd.
Lauryl betaine aqueous solution (30%): Obazolin LB-SF (trade mark) from Toho Chemical Industry Co., Ltd.
PPG-2 Cocamide: Amizett 1PC (trade mark) from Kawaken Fine Chemicals Co., Ltd.
Sodium laureth sulfate (30%): Alscope TH-330 (trade mark) from Toho Chemical Industry Co., Ltd.
Sodium cocoyl methyl taurate (30%): Neoscoap CN-30SF (trade mark) from Toho Chemical Industry Co., Ltd.
Glycol distearate: GENAPOL PMS (trade mark) from Clariant (Japan) K.K.
Pentylene glycol: DIOL PD (trade mark) from Kokyu Alcohol Kogyo Co., Ltd.
Stearamidopropyl Dimethylamine: Catinal MPAS (trade mark) from Toho Chemical Industry Co., Ltd.
Highly polymerized methyl polysiloxane (1): BY 22-029 (trade mark) from Dow Corning Toray Co., Ltd.
Hydrogenated castor oil isostearate, RISOCAST MIS (trade mark) from Kokyu Alcohol Kogyo Co., Ltd.
Polyglyceryl-2 isononanoate/dimer dilinoleate copolymer: HAILUCENT INDA II (trade mark) from Kokyu Alcohol Kogyo Co., Ltd.
Bis-ethoxydiglycol succinate: HAIAQUEOUSTER DCS (trade mark).from Kokyu Alcohol Kogyo Co., Ltd.
*Olea europaea* (olive) fruit oil: Olive oil from Kaneda Co., Ltd.
*Camellia japonica* seed oil: SHIMA TSUBAKI (trade mark) from JA Tokyo Tosho Toshima Branch.
*Macadamia ternifolia* seed oil: NIKKOL *Macadamia* nut oil (trade mark) from Nikko Chemicals Co., Ltd.
Cetyl alcohol: CETANOL NX (trade mark) from Kokyu Alcohol Kogyo Co., Ltd.
Stearyl alcohol: STEARYL ALCOHOL NX (trade mark) from Kokyu Alcohol Kogyo Co., Ltd.
Cetearyl alcohol: CETOSTEARYL ALCOHOL (trade mark) from Kokyu Alcohol Kogyo Co., Ltd.
Hydrogenated rapeseed alcohol: ALCOHOL NO. 20-B (trade mark) from Kokyu Alcohol Kogyo Co., Ltd.
Behenyl alcohol: BEHENYL ALCOHOL 65 (trade mark) from Kokyu Alcohol Kogyo Co., Ltd.
Dipropylene glycol (DPG): DPG-RF (trade mark) from Kuraray Co., Ltd.
Steartrimonium chloride: Genamin STAC (trade mark) from Clariant (Japan) K.K.
Distearyldimonium chloride: Genamin DSAC (trade mark) from Clariant (Japan) K.K.
Behentrimonium chloride: Genamin KDM-P (trade mark) from Clariant (Japan) K.K.
Dicocodimonium chloride: Pyonin B-2211 (trade mark) from Takemoto Oil & Fat Co., Ltd.
Amodimethicone: SF 8452 C (trade mark) from Dow Corning Toray Co., Ltd.
Cyclomethicone: SH 245 Fluid (trade mark) from Dow Corning Toray Co., Ltd.
Dimethicone: TSF451-10A (trade mark) from Momentive Performance Materials Japan LLC.
Phenoxyethanol: Hysorb EPH (trade mark) from Toho Chemical Industry Co., Ltd.
Hydroxyethylcellulose: HEC (trade mark) from Sumitomo Seika Chemicals Co., Ltd.
Hydroxypropyl methylcellulose: Metolose 60SH-4000 (trade mark) from Shin-Etsu Chemical Co., Ltd.
Ammonium acryloyldimethyltaurate/VP copolymer: Aristoflex AVC (trade mark) from Clariant (Japan) K.K.
Pentylene glycol: DIOL PD (trade mark) from Kokyu Alcohol Kogyo Co., Ltd.
1,3-Butylene glycol (BG): HAISUGARCANE BG (trade mark) from Kokyu Alcohol Kogyo Co., Ltd.
Polyquaternium-7: Lipoflow MN (trade mark) from Lion Corporation
Hydrolyzed silk: Promois Silk-1000Q (trade mark) from Seiwa Kasci Co., Ltd.

Highly polymerized methyl polysiloxane (1): BY 22-029 (trade mark) from Dow Corning Toray Co., Ltd.
Hydrogenated castor oil dimer dilinoleate: RISOCAST DA-H (trade mark) from Kokyu Alcohol Kogyo Co., Ltd.
Polyglyceryl-2 isostearate/dimer dilinoleate copolymer: HAILUCENT ISDA (trade mark) from Kokyu Alcohol Kogyo Co., Ltd.
Diglycerin/dilinoleic acid/hydroxystearic acid copolymer: RISOCAST HSDA (trade mark) from Kokyu Alcohol Kogyo Co., Ltd.
Diethylhexyl succinate: KAK DIOS (trade mark) from Kokyu Alcohol Kogyo Co., Ltd.
Polyglyceryl-2 isostearate: RISOREX PGIS21 (trade mark) from Kokyu Alcohol Kogyo Co., Ltd.
Glyceryl stearate: Poem V-100 (trade mark) from Riken Vitamin Co., Ltd.
Steareth-6: EMALEX 606 (trade mark) from Nihon Emulsion Co., Ltd.
*Euphorbia cerifera* (candelilla) wax: Candelilla wax SP-75 (trade mark) from Strahl & Pitsch Inc.
Ceresin: Ceresin #810 (trade mark) from Nikko Rica Corporation.
Microcrystalline wax: Purified microcrystalline wax from Nikko Rica Corporation.
Diisostearyl malate, Bis-dioctadecylamide dimer dilinoleic acid/ethylenediamine copolymer: HAIMALATE PAM (trade mark) from Kokyu Alcohol Kogyo Co., Ltd.
Cetearyl alcohol: CETOSTEARYL ALCOHOL (trade mark) from Kokyu Alcohol Kogyo Co., Ltd.
Dimethicone: TSF451-10A (trade mark) from Momentive Performance Materials Japan Co., Ltd.
Hydroxyethylcellulose: HEC (trade mark) from Sumitomo Seika Chemicals Co., Ltd.
Sodium stearoyl glutamate: Amisoft HS-11P (trade mark) from Ajinomoto Co., Inc.
Carbomer: Carbopol ETD 2050 (trade mark) from Nikko Chemicals Co., Ltd.
Potassium hydroxide
Bis-ethoxydiglycol succinate: HAIAQUEOUSTER DCS (trade mark) from Kokyu Alcohol Kogyo Co., Ltd.
*Simmondsia chinensis* (jojoba) seed oil: ECO OIL RS (trade mark) from Kokyu Alcohol Kogyo Co., Ltd.
Isododecane: MARUKASOL R (trade mark) from Maruzen Petrochemical Co., Ltd.
Light liquid isoparafin: IP Solvent 2028MU (trade mark) from Idemitsu Kosan Co., Ltd.
Dipropylene glycol (DPG): DPG-RF (trade mark) from Kuraray Co., Ltd.
Ethylhexyl methoxycinnamate: ESCALOL 557 (trade mark) from ISP Japan Ltd.
Tocopherol acetate: Tocopherol acetate from Eisai Food & Chemical Co., Ltd.
Octyldodecanol: RISONOL 20SP from Kokyu Alcohol Kogyo Co., Ltd.

The storage stability, ease of slip, absence of grittiness and safety to the skin in each of the cosmetics prepared in the Examples and the Comparative Examples were determined as follows:

Storage Stability

Damaged hair improving agents, shampoos, hair treatments, hair waxes, and hair oils, as indicated in the Examples and the Comparative Examples were prepared in accordance with the predetermined process. Three samples were prepared per each Example. Then, two of the samples were stored in a temperature-controlled bath, one at 25 degrees C. and the other at 45 degrees C., for one month. Remaining one of the samples was maintained successively at −10 degrees C., 25 degrees C. and 45 degrees C., each for 8 hours and then successively at 45 degrees C., 25 degrees C. and −10 degrees C., each for 8 hours in a temperature-controlled room. It took 48 hours per one operation. This sequential operation was repeated 5 times. The samples thus obtained were observed in respect to deterioration of appearance (occurrence of bulky particles), coloration, smelliness and separation by organoleptic assessments. As a result, in all samples, no deterioration of appearance, no coloration and no smelliness were observed. Therefore, the evaluation of storage stability was carried out only with regard to separation. Each sample was observed by eyes, and then, when there was no separation in all samples, the cosmetic was rated as "G". When the sample at one of the temperatures showed separation even if it was slight, the cosmetic was rated as "M". When the samples at two or more of the temperatures showed separation, even if it was slight, the cosmetic was rated as "B".

Ease of Slip and Absence of Grittiness

Root-trimmed healthy black human hair (100%) bundles (BS-B3N (trade mark) from Beaulax Co.) were used as test hair. First, sodium polyoxyethylene (3) laurylether sulfate aqueous solution (Emal 327 (trade mark) manufactured by Kao Corporation, 30 mass % aqueous solution) was diluted to prepare 2 mass % aqueous solution. The solution was then heated to 40° C., in which the test hair was immersed for 30 minutes. After it was washed with warm water at about 40° C. for 2 minutes, the excess water on it was removed with paper. The test hair was then dried using a dryer (Plajet PJ-208A (trade mark) manufactured by Ishizaki Electric Mfg. Co., Ltd). Brushing was repeated 100 times during drying in the hot air at about 70° C. with a distance of about 30 cm between the dryer and the hair. The test hair treated with hot air was bleached with a bleaching agent (Palty Mecha Flash Bleach (trade mark) from DARIYA Corporation) and was subsequently allowed to stand for 30 minutes at room temperature. Then the process as described above, from the immersion in sodium polyoxyethylene (3) laurylether sulfate aqueous solution to the bleach treatment, was repeated five times. Then the additional process from the immersion in sodium polyoxyethylene (3) laurylether sulfate aqueous solution to the drying step was repeated once. Bundles of the test hair thus treated were used as samples to evaluate "ease of slip" and "absence of grittiness".

Each sample of the hair bundles was coated uniformly with 0.2 ml of each damaged hair improving agents (shampoos, hair treatments, hair waxes, and hair oils) of Examples and Comparative Examples using a paddle. In the case of shampoos and hair treatments, the bundles were rinsed with running water for about 15 seconds after coating. The hair bundles were then dried using a dryer (Plajet PJ-208A (trade mark) manufactured by Ishizaki Electric Mfg. Co., Ltd). Brushing was repeated 50 times during drying in the hot air at about 70° C. with a distance of about 30 cm between the dryer and the hair. Then, 100 strands of hair were arbitrarily collected from each of the hair bundles, and were aligned at the roots, and thus were arranged uniformly on a cross-section paper to prepare a hair sample for measurement in a rectangular shape with dimensions 10 mm (width) and 50 mm (length: longitudinal direction of the hair). In order to evaluate "ease of slip" and "absence of grittiness", a friction tester (KES-SE Friction Tester (trade mark) manufactured by Kato Tech Co., Ltd, measuring condition; temperature: 253° C., load: 25 g, sensing station: silicone contact member) was used to measure "mean coefficient of friction (MIU)" and "deviation of the coefficient of friction (MMD)". The measurement was repeated three times and the measured values were averaged for evaluation. The mean coefficient of friction (MIU) was taken as a measure of ease of slip, and the deviation of the coefficient of friction (MMD) was taken as a measure of absence of grittiness. For the ease of slip, "G" indicates "good" for an MIU in the range of 0.20 or less, "M" indicates "Medium" for an MIU in the range of more than 0.20 and less than or equal to 0.40, and "B" indicates "Bad" for an MIU in the range of more than 0.40. For the absence of grittiness, "G" indicates "good" for an MMD in the range of 0.004 or less, "M" indicates "Medium" for an MMD in the range of more than 0.004 and less than or equal to 0.006, and "B" indicates "Bad" for an MMD in the range of more than 0.006.

Safety to the Skin

Subjects were twenty people, i.e. ten males and ten females. 0.05 g of each cosmetic obtained in the Examples or the Comparative Examples was applied to a circular patch with cotton lint of 1.0 cm diameter, which patch was applied to the forearm flexor of each subject and left for 24 hours. The patch was removed and the skin was examined 1 hour later and 24 hours later to rate the skin conditions of each subject according to the following criteria. When the results 1 hour later and 24 hours later were different, the stronger response was used for rating. When the 20 subjects exhibited (−), the rating was "G", when 1 to 2 subjects exhibited (+−) and the other subjects exhibited (−), the rating was "M"; and when three or more subjects exhibited (+−) and the other subjects exhibited (−) or when one or more subjects exhibited (+) to (+++), the rating was "B". For a hair treatment, aqueous 0.5% solution was used.

| Rating Criteria | |
|---|---|
| Skin Conditions | Rating |
| Erythema, edema, and blister | (+++) |
| Erythema and edema | (++) |
| Erythema | (+) |
| Slight erythema | (+−) |
| No erythema and no edema | (−) |

Example 1 to 3

Shampoo

Polyquaternium-10 and purified water were added to each of the compounds (A), ester compounds, of Synthesis Examples 1, 2, and 5, and the mixture was heated to 80° C. with stirring. While the temperature is being held at 80° C., polyglyceryl-10 isostearate and polyglyceryl-10 laurate were then added with stirring. Subsequently, lauryl betaine aqueous solution (30%) was added while the temperature is being held at 80° C., and was dispersed with an agitator at 1000 rpm for one minute with care to avoid foaming. PPG-2 Cocamide was subsequently added to the resulting mixture while the temperature was being held at 80° C. Then the components listed in Table 2 were added in the order of description from the top. The resulting mixture was cooled to 30° C. with stirring to prepare a shampoo.

Comparative Example 1

Shampoo

The process of Example 1 was performed except that the ester compound in Comparative Synthesis Example 2 was used in place of the component (A).

Table 2 shows the results of Examples 1 to 3 and Comparative Example 1. All the numerical values in Table 2 and the following Tables 3 to 5 are represented in unit of % by mass.

TABLE 2

| | Component | Ex. 1 | Ex. 2 | Ex. 3 | Comp. Ex. 1 |
|---|---|---|---|---|---|
| (A) | Ester Compound of Syn. Ex. 1 | 0.50 | — | — | — |
| | Ester Compound of Syn. Ex. 2 | — | 2.00 | — | — |
| | Ester Compound of Syn. Ex. 5 | — | — | 0.50 | — |
| (Com. A) | Ester Compound of Comp. Syn. Ex. 2 | — | — | — | 0.50 |
| (B) | Isostearyl neopentanoate | 0.20 | 1.00 | — | 0.20 |
| (D) | Squalane | — | — | 0.50 | — |
| Other Component | Polyquaternium-10 | 1.00 | 0.80 | 0.80 | 1.00 |
| | Polyglyceryl-10 isostearate | 1.50 | 1.50 | 1.50 | 1.50 |
| | Polyglyceryl-10 laurate | 1.00 | 1.00 | 1.00 | 1.00 |
| | Lauryl betaine aqueous solution (30%) | 10.00 | 10.00 | 8.00 | 10.00 |
| | PPG-2 Cocamide | 4.00 | 5.00 | 3.00 | 4.00 |
| | Sodium laureth sulfate (30%) | 23.00 | 25.00 | 30.00 | 23.00 |
| | Sodium cocoyl methyl taurate (30%) | 27.00 | 25.00 | 18.00 | 27.00 |
| | Ethylene glycol distearate | 2.00 | 1.50 | 2.00 | 2.00 |
| | Pentylene glycol | 3.00 | 4.00 | 3.00 | 3.00 |
| | Citric acid | 0.30 | 0.30 | 0.40 | 0.30 |
| | Stearamidopropyl Dimethylamine | 0.10 | — | — | 0.10 |
| | Highly polymerized methyl polysiloxane (1) | 0.20 | — | — | 0.20 |
| | Purified water | 26.20 | 22.90 | 31.30 | 26.20 |
| | Perfume | — | q.s. | q.s | — |
| | Total | 100.00 | 100.00 | 100.00 | 100.00 |
| Results of Evaluation | Storage stability | G | G | G | G |
| | Effect on damaged hair (ease of slip) | G | G | G | B |
| | Effect on damaged hair (absence of grittiness) | G | G | G | B |
| | Safety to skin | G | G | G | B |

The shampoo in Example 1 was prepared with the ester compound of Synthesis Example 1 as a component (A) and isostearyl neopentanoate as a component (B). Effects on damaged hair, i.e. ease of slip and absence of grittiness, were both rated as "good". The storage of stability and safety to the skin were also rated as "good". In Example 2, the ester compound of Synthesis Example 2 and isostearyl neopentanoate were used as a component (A) and as a component (B), respectively, where the amounts of these compounds were increased relative to those in Example 1. Both ease of slip and absence of grittiness were rated as "good". In Example 3, the ester compound of Synthesis Example 5 and squalane were used as a component (A) and as a component (D), respectively. Both ease of slip and absence of grittiness were rated as "good". The use of the component (D), squalane, provided the good result even without the use of the component (B) or the component (C).

In Comparative Example 1, the ester compound of Comparative Synthesis Example 2 was used in place of the component (A), ester compound of Synthesis Example 1 used in Example 1. Either ease of slip or absence of grittiness was not rated as "good".

Example 4 to 7

Hair Treatment

Each of the components in Composition (I) and Composition (II) indicated in Table 3 was independently dissolved homogenously at a temperature in the range of 75° C. to 80° C. Then Composition (I) was added to Composition (II) with stirring and subsequently emulsified with a homoblender. Then, Component (III) was added to the resulting emulsion with stirring, and the resulting mixture was then cooled to 30° C. with stirring to prepare a hair treatment. The results of evaluation are shown in Table 3.

Comparative Example 2

Hair Treatment

The process of Example 4 was performed except that the ester compound of Comparative Synthesis Example 2 was used in place of the compound (A).

Table 3 shows the results of Examples 4 to 7 and Comparative Example 2.

TABLE 3

| | | Component | Ex. 4 | Ex. 5 | Ex. 6 | Ex. 7 | Comp. Ex. 2 |
|---|---|---|---|---|---|---|---|
| (I) | (A) | Ester Compound of Syn. Ex. 1 | 2.00 | — | — | 2.50 | — |
| | | Ester Compound of Syn. Ex. 2 | — | 10.00 | 3.00 | — | — |
| | | Ester Compound of Syn. Ex. 5 | — | — | — | 1.50 | — |
| | (Comp. A) | Ester Compound of Comp. Syn. Ex. 2 | — | — | — | — | 2.00 |
| | (B) | Polyglyceryl-2 triisostearate | — | 1.00 | — | — | — |
| | | Triisostearin: | — | 1.00 | — | — | — |
| | | Dipentaerythrityl hexaisostearate | — | — | 2.00 | — | — |
| | | Cetyl ethylhexanoate | — | — | — | 1.00 | — |
| | (C) | Isostearyl alcohol | 0.50 | — | — | — | 0.50 |
| | (D) | Squalane | — | — | 1.00 | — | — |
| | Other Components | Triethylhexanoin | — | — | — | 1.00 | — |
| | | Hydrogenated castor oil isostearate | 2.00 | — | — | — | 2.00 |
| | | Polyglyceryl-2 isononanoate/dimer dilinoleate copolymer | 2.00 | 1.00 | 2.00 | — | 2.00 |
| | | Bis-ethoxydiglycol succinate | — | — | — | 2.00 | — |
| | | *Olea europaea* (olive) fruit oil | 1.00 | — | — | — | 1.00 |
| | | *Camellia japonica* seed oil | — | — | 1.00 | — | — |
| | | *Macadamia ternifolia* seed oil | — | — | — | 1.50 | — |
| | | Cetanol | 4.00 | — | — | — | 4.00 |
| | | Stearyl alcohol | — | — | — | 3.00 | — |
| | | Cetearyl alcohol | — | 2.00 | — | — | — |
| | | Hydrogenated rapeseed alcohol | — | 2.00 | 2.00 | — | — |
| | | Behenyl alcohol | 1.00 | — | 1.00 | 1.50 | 1.00 |
| | | Dipropylene glycol | 4.00 | — | 3.00 | 3.00 | 4.00 |
| | | Steartrimonium chloride | 1.00 | — | — | 1.00 | 1.00 |
| | | Distearyldimonium chloride | — | 1.00 | 1.00 | 1.00 | — |
| | | Behentrimonium chloride | — | — | 0.50 | — | — |
| | | Dicocodimonium chloride | — | 1.00 | 1.00 | — | — |
| | | Amodimethicone | 0.50 | — | — | 0.20 | 0.50 |
| | | Cyclomethicone | — | — | 1.00 | 2.00 | — |
| | | Dimethicone | 2.00 | — | 2.00 | — | 2.00 |
| | | Phenoxyethanol | — | — | 0.10 | — | — |
| (II) | | Hydroxyethylcellulose | 0.30 | — | — | 0.20 | 0.30 |
| | | Hydroxypropyl methylcellulose | — | — | 0.20 | — | — |
| | | Ammonium acryloyldimethyl-taurate/VP copolymer | — | 0.30 | 0.20 | 0.10 | — |
| | | Pentylene glycol | 3.00 | 3.00 | — | — | 3.00 |
| | | Butylene glycol | — | 1.00 | 3.00 | — | — |
| | | Polyquaternium -7 | — | — | 1.00 | — | — |
| | | Hydrolyzed silk | 0.01 | — | — | 0.02 | 0.01 |
| | | Glycollic acid | 0.50 | — | — | 1.00 | 0.50 |

TABLE 3-continued

|  | Component | Ex. 4 | Ex. 5 | Ex. 6 | Ex. 7 | Comp. Ex. 2 |
|---|---|---|---|---|---|---|
|  | Methylparaben | — | — | 0.15 | 0.20 | — |
|  | Purified water | 74.69 | 76.70 | 74.85 | 76.48 | 74.69 |
| (III) | Highly polymerized methyl polysiloxane (1) | 1.50 | — | — | 0.80 | 1.50 |
|  | Total | 100.00 | 100.00 | 100.00 | 100.00 | 100.00 |
| Results of Evaluation | Storage stability | G | G | G | G | G |
|  | Applicability (Ease of Spreading, absence of slippery feel) | G | G | G | G | B |
|  | Effect on dammaged hair (ease of slip) | G | G | G | G | B |
|  | Effect on dammaged hair (absence of grittiness) | G | G | G | G | B |
|  | Safety to skin | G | G | G | G | B |

The hair treatment in Example 4 was prepared with the ester in Synthesis Example 1 as a component (A) and the isostearyl alcohol as a component (C). Effects on damaged hair, i.e. ease of slip and absence of grittiness, were both rates as "good". The storage of stability and safety to the skin were also rated as "good". Thus, the use of the component (C) provided the good result. In Example 5, the ester compound of Synthesis Example 2 was used as a component (A), and polyglyceryl-2 triisostearate and tri-isostearin were used as components (B). Both ease of slip and absence of grittiness were also rated as "good". In Example 6, the ester compound of Synthesis Example 2, dipentaerythrityl hexaisostearate, and squalane were used as a component (A), a component (B), and a component (D), respectively. Both ease of slip and absence of grittiness were rated as very "good". In Example 7, the ester compounds of Synthesis Example 1 and Synthesis Example 5 were used as compounds (A), and cetyl ethylhexanoate was used as a compound (B). Both ease of slip and absence of grittiness were also rated as "good".

In Comparative Example 2, the ester compound of Synthesis Comparative Example 2 was used in place of the component (A), ester compound of Synthesis Example 1, in Example 4. Both ease of slip and absence of grittiness were rated as "bad".

Example 8 to 11

Hair wax

Each of the components in Composition (I) and Composition (II) indicated in Table 4 was independently dissolved homogenously at a temperature in the range of 75° C. to 80° C. Composition (I) was then added to Composition (II) with stirring and subsequently emulsified with a homomixer. The resulting mixture was then cooled to 30° C. with stirring to prepare a hair wax. The results of evaluation are shown in Table 4.

Comparative Example 3

Hair Wax

The process of Example 8 was performed except that the ester compound of Comparative Synthesis Example 3 was used in place of the component (A).

Table 4 shows the results of Examples 8 to 11 and Comparative Example 3.

TABLE 4

|  |  | Component | Ex. 8 | Ex. 9 | Ex. 10 | Ex. 11 | Comp. Ex. 3 |
|---|---|---|---|---|---|---|---|
| (I) | (A) | Ester Compound of Syn. Ex. 2 | 5.00 | 3.00 | — | — |  |
|  |  | Ester Compound of Syn. Ex. 3 | — | — | 2.00 | 1.00 |  |
|  |  | Ester Compound of Syn. Ex. 4 | — | — | — | 1.00 |  |
|  | (Comp. A) | Ester Compound of Comp. Syn. Ex. 3 | — | — | — | — | 5.00 |
|  | (B) | Polyglyceryl-2 tetraisostearate | — | — | 2.00 | — | — |
|  |  | Cetyl ethylhexanoate | — | 3.00 | — | — | — |
|  |  | Oleyl erucate | 1.00 | — | — | — | 1.00 |
|  |  | Isostearyl isostearate | — | 1.00 | — | — | — |
|  | (D) | Mineral oil | — | — | — | 2.00 | — |
|  | Other Components | Hydrogenated castor oil isostearate | — | 1.00 | 3.00 | — | — |
|  |  | Hydrogenated castor oil dimer dilinoleate | — | — | — | 1.00 | — |
|  |  | Polyglyceryl-2 isostearate/dimer dilinoleate copolymer | 4.00 | — | — | — | 4.00 |
|  |  | Polyglyceryl-2 isononanoate/dimer dilinoleate copolymer | — | 1.00 | — | — | — |
|  |  | Diglycerin/dilinoleic acid/hydroxystearic acid copolymer | — | — | 1.00 | 2.00 | — |
|  |  | Diethylhexyl succinate | — | — | 3.00 | — | — |
|  |  | Polyglyceryl-10 isostearate | 1.50 | — | — | 3.50 | 1.50 |
|  |  | Glyceryl stearate | 2.00 | — | — | — | 2.00 |
|  |  | Steareth-6 | — | — | — | — | — |
|  |  | *Euphorbia cerifera* (candelilla) wax | 4.00 | 5.00 | 5.50 | — | 4.00 |
|  |  | Ceresin | 3.00 | 4.00 | — | — | 3.00 |
|  |  | Microcrystalline wax | — | — | 2.00 | — | — |

TABLE 4-continued

|  | Component | Ex. 8 | Ex. 9 | Ex. 10 | Ex. 11 | Comp. Ex. 3 |
|---|---|---|---|---|---|---|
|  | Diisostearyl malate, Bis-dioctadecylamide dimer dilinoleic acid/ethylenediamine copolymer | — | — | — | 10.00 | — |
|  | Cetearyl alcohol | — | 1.00 | — | — | — |
|  | Behenyl alcohol | 2.50 | 2.00 | 2.00 | 2.50 | 2.50 |
|  | Pentylene glycol | 3.00 | 3.00 | — | 3.00 | 3.00 |
|  | Dimethicone | — | 1.00 | 2.00 | 2.00 | — |
| (II) | Hydroxyethylcellulose | 0.40 | — | — | — | 0.40 |
|  | Hydroxypropyl methylcellulose | — | — | — | 0.50 | — |
|  | Ammonium acryloyldimethyl-taurate/VP copolymer | — | 0.40 | — | — | — |
|  | Sodium stearoyl glutamate | — | — | — | 0.50 | — |
|  | Carbomer | — | — | 0.60 | 0.60 | — |
|  | Potassium hydroxide | — | — | 0.16 | 0.16 | — |
|  | Methylparaben | — | — | 0.15 | — | — |
|  | Purified water | 73.60 | 74.60 | 76.59 | 70.24 | 73.60 |
|  | Total | 100.00 | 100.00 | 100.00 | 100.00 | 100.00 |
| Results of Evaluation | Storage stability | G | G | G | G | G |
|  | Applicability (Ease of Spreading, absence of slippery feel) | G | G | G | G | M |
|  | Effect on dammaged hair (ease of slip) | G | G | G | G | B |
|  | Effect on dammaged hair (absence of grittiness) | G | G | G | G | M |
|  | Safety to skin | G | G | G | G | G |

The hair wax in Example 8 was prepared with the ester compound in Synthesis Example 2 as a component (A) and oleyl erucate as a component (B). Effects on damaged hair, i.e. ease of slip and absence of grittiness, were both rated as "good". The storage stability and safety to the skin were also rated as "good". In Example 9, the ester compound of Synthesis Example 2 was used as a component (A), and cetyl ethylhexanoate, and isostearyl isostearate were used as components (B). Both ease of slip and absence of grittiness were also rated as "good". In Example 10, the ester compound of Synthesis Example 3 and polyglyceryl-2 tetraisostearate were used as a component (A) and as a component (B), respectively. Both ease of slip and absence of grittiness were also rated as "good". In Example 11, the ester compounds of Synthesis Example 3 and Synthesis Example 4 were used as compounds (A) and a mineral oil was used as a compound (D). The use of the component (D), mineral oil, provided the good result even without the use of the component (B) or component (C).

In Comparative Example 3, the ester compound of Comparative Synthesis Example 3 was used in place of the component (A), ester compound of Synthesis Example 2 used in Example 8. Neither ease of slip or absence of grittiness was rated as "good".

Examples 12 to 15

Hair Oil

Each of the components indicated in Table 5 was dissolved homogenously at a temperature of 60° C. to 70° C. The resultant mixture was cooled to 30° C. with stirring to prepare a hair oil. Table 5 shows the results.

Comparative Example 4

Hair Oil

The process of Example 13 was performed except that the ester compound of Comparative Synthesis Example 3 was used in place of the component (A).

Table 5 shows the results of Examples 12 to 15 and Comparative Example 4.

TABLE 5

|  | Component | Ex. 12 | Ex. 13 | Ex. 14 | Ex. 15 | Comp. Ex. 4 |
|---|---|---|---|---|---|---|
| (A) | Ester Compound of Syn. Ex. 2 | 30.00 | — | — | 1.00 | — |
|  | Ester Compound of Syn. Ex. 3 | — | 0.50 | — | — | — |
|  | Ester Compound of Syn. Ex. 4 | — | 0.50 | — | — | — |
|  | Ester Compound of Syn. Ex. 5 | — | — | — | 2.00 | — |
|  | Ester Compound of Syn. Ex. 7 | — | — | — | 1.00 | — |
|  | Ester Compound of Syn. Ex. 8 | — | — | 15.00 | — | — |
| (Comp. A) | Ester Compound of Comp. Syn. Ex. 3 | — | — | — | — | 1.00 |
| (B) | Pentaerythrityl tetraisostearate | 4.00 | — | — | — | — |
|  | Hexyldecyl isostearate | — | 2.00 | — | — | 2.00 |
|  | Isostearyl neopentanoate | — | 10.00 | — | — | 10.00 |
|  | Dipentaerythrityl hexaisostearate | — | — | 3.00 | — | — |
|  | Ethylhexyl hydroxystearate | 1.00 | — | — | — | — |
| (D) | Mineral oil | — | — | — | 5.00 | — |
| Other Components | Bis-ethoxydiglycol succinate | — | — | 2.00 | — | — |
|  | Benzyl alcohol | — | — | — | 1.00 | — |
|  | Octyldodecanol | — | 1.00 | — | — | 1.00 |
|  | *Simmondsia chinensis* (jojoba) seed oil | — | 1.00 | — | — | 1.00 |
|  | *Camellia japonica* seed oil | — | 1.00 | 1.00 | — | 1.00 |

TABLE 5-continued

| | Component | Ex. 12 | Ex. 13 | Ex. 14 | Ex. 15 | Comp. Ex. 4 |
|---|---|---|---|---|---|---|
| | Isododecane | 54.90 | 64.50 | 38.00 | — | 64.50 |
| | Light liquid isoparafin | — | — | 20.90 | 72.00 | — |
| | Ethanol | 10.00 | 13.00 | 15.00 | 15.00 | 13.00 |
| | Dipropylene glycol | — | 2.00 | — | — | 2.00 |
| | Pentylene glycol | — | 3.00 | — | — | 3.00 |
| | Butylene glycol | — | — | 2.00 | — | — |
| | Cyclomethicone | — | — | 1.00 | — | — |
| | Dimethicone | — | — | 2.00 | 3.00 | — |
| | Ethylhexyl methoxycinnamate | — | 1.50 | — | — | 1.50 |
| | Tocopherol acetate | 0.10 | — | 0.10 | — | — |
| | Perfume | — | — | q.s. | q.s | — |
| | Total | 100.00 | 100.00 | 100.00 | 100.00 | 100.00 |
| Results of Evaluation | Storage stability | G | G | G | G | G |
| | Applicability (Ease of Spreading, absence of slippery feel) | G | G | G | G | M |
| | Effect on dammaged hair (ease of slip) | G | G | G | G | B |
| | Effect on dammaged hair (absence of grittiness) | G | G | G | G | M |
| | Safety to skin | G | G | G | G | G |

The hair oil in Example 12 was prepared with the ester in Synthesis Example 2 as a component (A), and pentaerythrityl tetraisostearate and ethylhexyl hydroxystearate as components (B). Effects on damaged hair, i.e. ease of slip and absence of grittiness, were both rated as "good". The storage stability and safety to the skin were also rated as "good". In Example 13, the ester compounds of Synthesis Examples 3 and 4 were used as components (A), and hexyldecylisostearate and isostearyl neopentanoate were used as components (B). Both ease of slip and absence of grittiness were also rated as "good". In Example 14, the ester compound of Synthesis Example 8 and dipentaerythrityl hexaisostearate as a component (A) and a component (B), respectively. Similarly, both ease of slip and absence of grittiness were also rated as "good". In Example 15, the ester compounds of Synthesis Examples 2, 5, and 7 were used as the components (A), and a mineral oil was used as the compound (D). With regard to a hair oil, the use of the component (D), mineral oil, also provided the good result even without the use of the component (B) or component (C).

In Comparative Example 4, the ester compound of Comparative Synthesis Example 3 was used in place of the compounds (A), the ester compounds of Synthesis Examples 3 and 4 in Example 13. Neither ease of slip or absence of grittiness was rated as "good".

INDUSTRIAL APPLICABILITY

The damaged hair improving agent of the invention and the process for improving damaged hair using the same impart sleek fell to damaged hair and reduce gritty feel of the damaged hair to impart smooth feel to the damaged hair. Accordingly, the damaged hair improving agent is highly expected for use in cosmetics such as shampoos, hair treatments, hair waxes, and hair oils.

The invention claimed is:

1. A damaged hair improving agent comprising: (A) ester compounds made by esterifying dipentaerythritol only with isononanoic acid, the molar ratio of the dipentaerythritol residue to the isononanoic acid residue ranging from 1.0:3.0 to 1.0:6.0, the ester compounds comprising at least two esters selected from monoester, diester, triester, tetraester, pentaester, and hexaester of dipentaerythritol and isononanoic acid, and one or more substances selected from the group consisting of (B) an ester compound having a linear or branched alkyl or alkenyl group having 16 to 18 carbon atoms wherein hydrogen atoms on these groups are optionally replaced with hydroxyl groups, and a viscosity of 2,000 mPa·s or less at 25° C., wherein the ester compound (B) is exclusive of the ester compounds of (A), (C) an alcohol having a linear or branched alkyl or alkenyl group having 16 to 18 carbon atoms and a viscosity of 2,000 mPa·s or less at 25° C., and (D) hydrocarbon oil having at least 20 carbon atoms.

2. The damaged hair improving agent according to claim 1, wherein the molar ratio of the dipentaerythritol residue to the isononanoic acid residue in the component (A) ranges from 1.0:3.5 to 1.0:6.0.

3. The damaged hair improving agent according to claim 1, wherein the molar ratio of the dipentaerythritol residue to the isononanoic acid residue in the component (A) ranges from 1.0:4.0 to 1.0:6.0.

4. The damaged hair improving agent according to claim 1, wherein the component (B) is selected from the group consisting of isostearyl neopentanoate, polyglyceryl-2 triisostearate, triisostearin, cetyl ethylhexanoate, polyglyceryl-2 tetraisostearate, oleyl erucate, isostearyl isostearate, pentaerythrityl tetraisostearate, dipentaerythrityl hexaisostearate, hexyldecylisostearate, and ethylhexyl hydroxystearate.

5. The damaged hair improving agent according to claim 1, comprising at least one substance selected from the group consisting of the component (B), the component (C), and the component (D), in an amount of 10 to 1,200 parts by mass in total of the components of (B), (C) and (D) relative to 100 parts by mass of the component (A).

6. The damaged hair improving agent according to claim 1, comprising at least one substance selected from the group consisting of the component (B), the component (C), and the component (D), in an amount of 10 to 1,000 parts by mass in total of the components of (B), (C) and (D) relative to 100 parts by mass of the component (A).

7. The damaged hair improving agent according to claim 1, comprising at least one substance selected from the group consisting of the component (B), the component (C), and the component (D), in an amount of 10 to 150 parts by mass in total of the components of (B), (C) and (D) relative to 100 parts by mass of the component (A).

8. The damaged hair improving agent according to claim 1, comprising at least one substance selected from the group consisting of the component (B), the component (C), and the component (D), in an amount of 20 to 100 parts by mass in total of the components of (B), (C) and (D) relative to 100 parts by mass of the component (A).

9. The damaged hair improving agent according to claim 1, wherein the component (C) is isostearyl alcohol.

10. The damaged hair improving agent according to claim 1, wherein the component (D) is selected from the group of squalane and mineral oil.

* * * * *